United States Patent [19]

Chiang

[11] Patent Number: 5,095,113
[45] Date of Patent: Mar. 10, 1992

[54] PREPARATION OF METHYL-1,3-5-TRIAZINES

[75] Inventor: George C. Chiang, Wilmington, Del.

[73] Assignee: E. I. du Pont de Nemours and Company, Wilmington, Del.

[21] Appl. No.: 692,405

[22] Filed: Apr. 26, 1991

[51] Int. Cl.$^5$ .................. C07D 251/42; C07D 251/16
[52] U.S. Cl. ...................................... 544/194; 544/217
[58] Field of Search ................................. 544/194, 217

[56] References Cited
U.S. PATENT DOCUMENTS 4,886,881 12/1989 Chiang .............................. 544/194
4,933,450 6/1990 Chiang .............................. 544/194

Primary Examiner—John M. Ford
Attorney, Agent, or Firm—James A. Costello

[57] ABSTRACT

A method for making methyl-1,3,5-triazines including the 2,4-dichloro-6-methyl- and the 2-methyl-4-methylamino-6-methoxy-1,3,5-triazines, comprising reacting sodium dicyanamide with a cyclizing agent in the presence of HCl to make the 2,4-dichloro-6-methyl-triazine and reacting said triazine, additionally, with sodium methoxide and monomethylamine to make the 2-methyl-4-methylamino-6-methoxytriazine.

14 Claims, No Drawings

PREPARATION OF METHYL-1,3-5-TRIAZINES

BACKGROUND OF THE INVENTION

1. Field of the Invention

This invention is directed to a method for preparing methyl-1,3,5-triazines, preferably without isolation of intermediate byproducts.

2. State of the Art

Z. Anorg. Allg. Chemie. Bd. 322, 1963, pages 265 to 274, discloses the preparation of N-cyanochloroformamide from sodium dicyanamide. WO 81/03020 discloses a procedure for the synthesis of 1,3,5-triazines. Dyes and Pigments, (1986), 7(6), pages 419 to 443, discloses the synthesis of 2,4-dichloro-6-methyl-s-triazine by reacting N-cyanochloroformamidine with N,N-dimethylacetamide in the presence of phosphorus oxychloride. U.S. Pat. No. 3,361,746 discloses the synthesis of 2,4-dichloro-6-methyl-s-triazines. Synthesis (1981), page 907, and (1980), page 841, disclose the synthesis of triazines from N-cyanocarbamimidates and N-cyanoamidines, respectively, as does Aust. J. Chem., 1981, 34, pages 623 to 634.

East German Patents 70,296 and 71,768; Great Britain Patent 1,180,346; Rembarz et al., Wiss. Z. Univ. Rostock. Math.-Naturwiss. Reihe, 1972, 21(2) pages 93 to 100; and U.S. Pat. No. 2,418,476 each disclose transformation of zinc bis(dicyanimide) via zinc bis(imino-bis-carbimic acid methyl ester) to 2-methyl-4,6-dimethoxy-1,3,5-triazine.

U.S. Pat. No. 4,886,881 discloses a one-pot preparation of 2-aminotriazines from the reaction of dicyandiamides with trimethylorthoacetate in the presence of a catalyst. U.S. Pat. No. 4,933,450 discloses the preparation of 2-aminotriazines from zinc bis(imino-bis-carbimic acid methyl ester). U.S. Pat. No. 3,296,263 and Wiss. Z. Univ. Rostock, Math.-Naturwiss. Reihe, 1972, 21(2), pages 113 to 117 disclose the conversion of 2-methyl-4,6-dimethoxy-1,3,5-triazine to 2-methyl-4-methylamino-6-methoxy-1,3,5-triazine.

SUMMARY OF THE INVENTION

This invention pertains to a method for making a methyl-1,3,5-triazine comprising (Reaction A) reacting sodium dicyanamide with a cyclizing agent in the presence of HCl, wherein the cyclizing agent is selected from the group (i) acetyl chloride, and (ii) the halomethyleneinium salt formed from N-methylacetamide and phosphorus oxychloride or from N-methylacetamide and phosgene, the triazine being 2,4-dichloro-6-methyl-1,3,5-triazine.

This invention also pertains to a method for making 2-methyl-4-methylamino-6-methoxy-1,3,5-triazine comprising reacting the 2,4-dichloro-6-methyl-1,3,5-triazine from Reaction A with sodium methoxide and monomethylamine.

Preferred reaction conditions comprise forming the 2,4-dichloro-6-methyl-1,3,5-triazine from the sodium dicyanamide/HCl/cyclizing agent without isolation of any intermediates. Such "one-pot" process is characterized by high yields of both the 2,4-dichloro-6-methyl- and the 2-methyl-4-methylamino-6-methoxy-triazines.

Scheme I, hereafter, depicts formation of the dichlorotriazine (III). Scheme II depicts formation of the methylamino triazine (VI). Scheme III depicts the overall process for making VI in its preferred embodiment, that is, without intermediate isolation of III.

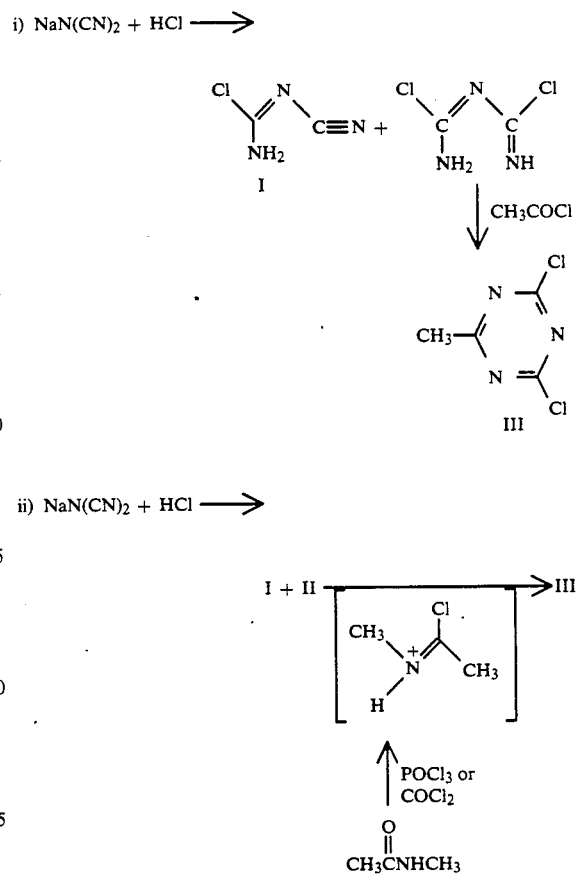

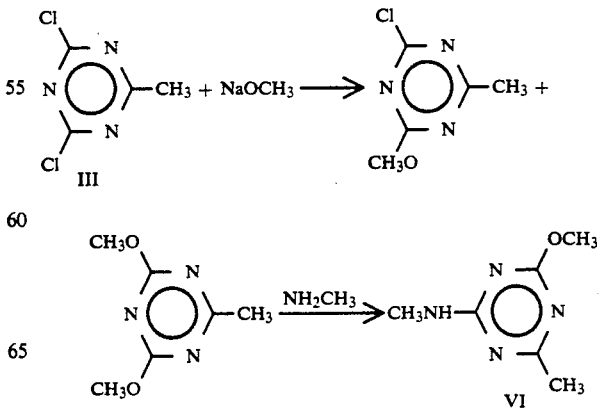

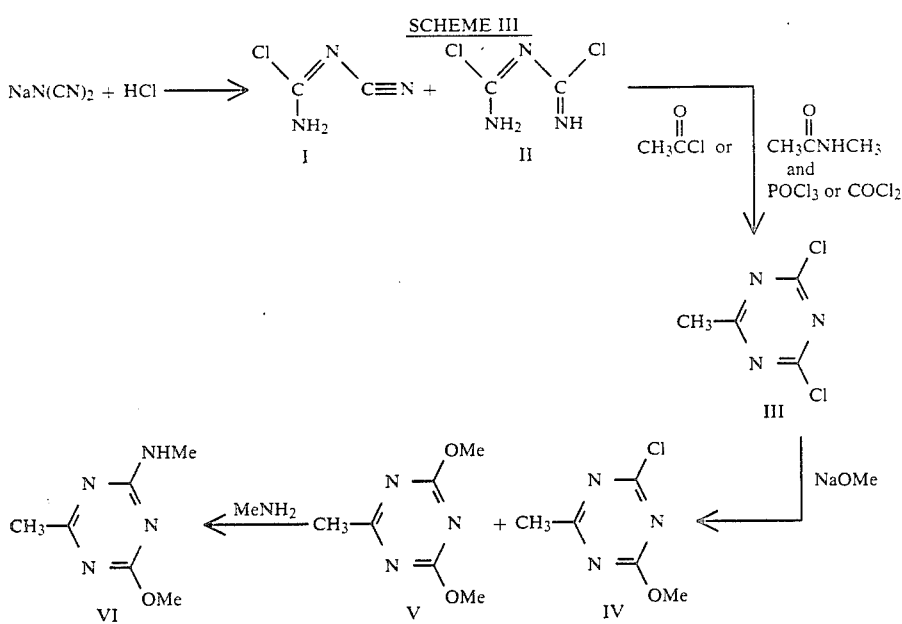

SCHEME III

The method of this invention is not limited to forming intermediates I, II, IV and/or V. The precise identity of I and II has not been absolutely proven and the presence of both IV and V will depend on the amount of NaOMe actually employed. Regardless what the intermediates are, it is characteristic of the most preferred embodiment of this invention that there are no intermediate isolations of any materials. Surprisingly, improved yields of III and VI are the result, provided further that HCl is employed in Reaction A.

Typical reaction conditions are as follows. The preferred solvents are substantially inert and are selected from hexane, methylene chloride, benzene, toluene, xylenes, monochlorobenzene, dichlorobenzene and methyl acetate. Toluene and methyl acetate are the most preferred solvents. Temperatures are 0° to 150° C. Preferred temperatures are 50° to 120° C. Reaction pressures are 1 to 5 atm. Preferred pressure is 1 atm. Reaction times are 0.5 to 48 hours, preferably 1 to 24 hours. The ratio of hydrochloric acid is 2 to 5 moles based on sodium dicyanamide. Preferred ratio of hydrochloric acid to sodium cyanamide is 2 to 4 moles.

DETAILS OF THE INVENTION

The process of Scheme I can be carried out by treating a solution of sodium dicyanamide with 2-5 equivalents of hydrochloric acid introduced as a gas. The use of 2-4 equivalents of hydrochloric acid is most economical. The reaction is usually carried out at or near room temperature. After stirring 0.1 to 2 hours, the resultant mixture is reacted with acetyl chloride or the halomethyleneinium salt derived from N-methylacetamide, conveniently prepared in-situ by the addition of N-methylacetamide and phosphorus oxychloride or phosgene.

The reaction mixture is heated for 1–4 hours, cooled, and 2,4-dichloro-6-methyl-1,3,5-triazine is isolated by conventional means. Alternatively, this product without isolation, can be treated with sodium methoxide, to give a mixture of IV and V. The use of excess sodium methoxide affords pure V. Without intermediate isolation, monomethylamine is added (approximately 3 equivalents relative to sodium dicyanamide) with cooling (10°–15° C.) to yield VI. The triazines formed by the process of this invention are useful intermediates for the manufacture of herbicides such as sulfonylureas.

The following Examples further illustrate the invention.

EXAMPLE 1

In a 500 ml flask equipped with a mechanical stirrer, a reflux condenser, a thermometer and a gas inlet was placed 25 g of sodium dicyanamide and 250 ml of toluene. At 25°–35° C., 31 g of HCl gas was introduced. The white slurry was stirred for an additional 15 minutes at room temperature. Then, 21 g of N-methylacetamide and 43.5 g of phosphorus oxychloride were charged. After stirring for 5 minutes, the reaction mixture was heated to 85° C. for 1.5 hours and then to 110° C. for an hour. It was cooled to 25° C. and then poured into 500 ml of ice water. After extraction with an additional 250 ml of toluene, the combined toluene extracts were dried over MgSO4, filtered and evaporated to give 26 g of 2,4-dichloro-6-methyl-1,3,5-triazine (58% yield) as white needles.

EXAMPLE 2

In a 2 l flask equipped with a mechanical stirrer, a dry ice condenser, a thermometer and a gas inlet was charged 700 ml of toluene and 50 g of N-methylacetamide. It was cooled to 10° C. and then was charged 60 g of phosgene at 10°–20° C. Afterwards, 30 g of HCl gas was introduced. Then, 50 g of sodium dicyanamide was charged in one portion and the HCl charge continued until 56 g of total HCl was introduced. The reaction mass was heated to 65° C. for 2 hours. After cooling to 20° C., the reaction content consisted of toluene and some tars. The toluene phase was decanted into 500 ml of ice water. The residue was rinsed with 300 ml of toluene and then decanted. The combined toluenes were washed with water (2×500 ml) and dried over MgSO4. After evaporation, 32.5 g of 2,4-dichloro-6-methyl-1,3,5-triazine was obtained as white needles (35% yield).

EXAMPLE 3

To a 1 l flask equipped with a mechanical stirrer, a reflux condenser, a thermometer and a gas inlet was charged 500 ml of methyl acetate and 50 g of sodium dicyanamide. At room temperature, 80 g of HCl gas was charged. After stirring for 15 minutes, 88 g of acetyl chloride was added in one portion. The reaction mixture was heated to reflux for 3 hours. It was then cooled to 10° C. and poured into 500 ml of ice water. Extraction with methyl acetate and subsequent drying and evaporation afforded 32 g of 2,4-dichloro-6-methyl-1,3,5-triazine. The yield was 37%.

EXAMPLE 4

To a 1 l flask equipped with a mechanical stirrer, a thermometer, a reflux condenser and a gas inlet tube was charged 50 g of sodium dicyanamide and 500 ml of toluene. HCl gas (80 G) was fed into the white slurry at 20°–30° C. over one hour. The resulting thick white slurry was stirred for half an hour at room temperature. Then 50 g of N-methylacetamide and 87 g of POCl3 were charged to the reactor. It was heated to 40° C. and an exotherm occurred which caused the temperature to rise to 65° C. It was heated for 2 hours at 65° C. During the heating, off-gas was scrubbed in a water scrubber. Upon cooling to 20° C., ice water (400 ml) was introduced and the stirring continued for a few minutes until all solids dissolved. Afterwards, the reactor contents were transferred to a 2-l separatory funnel for extraction. The water layer was extracted with another 500 ml of toluene. The combined toluene extracts were returned to a 2-l flask in an ice bath. At 5° C., 150 g of 25% NaOMe was dropped in over half an hour so that the reactor temperature was maintained between 5° C. and 20° C. At this time, GC showed complete disappearance of methyldichlorotriazine and formation of a mixture of 2-methyl-4,6-dimethoxy-1,3,5-triazine and 2-methyl-4-chloro-6-methoxy-1,3,5-triazine. Addition of more sodium methoxide (266 g total of 25% NaOMe) caused the exclusive formation of 2-methyl-4,6-dimethoxy-1,3,5-triazine. Addition of 500 ml of ice water and 130 g of 40% MeNH2 at 10° C. and continued stirring at 10°–15° C. for 2 hours caused the above clear solution to change into a white slurry. When GC analysis indicated all the 2-methyl-4,6-dimethoxytriazine was gone and 2-methyl-4-methylamino-6-methoxy-1,3,5-triazine was formed, the reaction mixture was filtered and the filter cake washed with water and dried in a vacuum oven overnight at 70° C. under nitrogen to yield 45 g of said triazine. The assay was >98.5%.

I claim:

1. A method for making a methyl-1,3,5-triazine comprising the steps of:
   (A) reacting sodium dicyanamide with a cyclizing agent in the presence of HCl, wherein the cyclizing agent is selected from the group (i) acetyl chloride and (ii) the halomethyleneinium salt formed from N-methylacetamide and one of phosphorus oxychloride or phosgene, the triazine being 2,4-dichloro-6-methyl-1,3,5-triazine; and
   (B) reacting the 2,4-dichloro-6-methyl-1,3,5-triazine with sodium methoxide and monomethylamine to form 2-methyl-4-methylamino-6-methoxy-1,3,5-triazine.

2. A method according to claim 1 comprising Reaction A for making 2,4-dichloro-6-methyl-1,3,5-triazine.

3. A method according to claim 1 conducted without isolation of intermediates for making 2-methyl-4-methylamino-6-methoxy-1,3,5-triazine.

4. A method according to claim 1 wherein the ratio of HCl is 2 to 5 moles with respect to sodium dicyanamide.

5. A method according to claim 1 wherein the cyclizing agent is acetyl chloride.

6. A method according to claim 1 wherein the cyclizing agent is the halomethyleneinium salt.

7. A method according to claim 6 wherein the salt is formed from N-methylacetamide and phosphorus oxychloride.

8. A method according to claim 5 wherein the solvent is methyl acetate.

9. A method according to claim 6 wherein the solvent is toluene.

10. A method according to claim 7 wherein the solvent is toluene.

11. A method according to claim 2 employing a ratio of HCl of 2 to 5 moles with respect to sodium dicyanamide.

12. A method according to claim 11 employing acetyl chloride as the cyclizing agent and methyl acetate as the solvent.

13. A method according to claim 11 employing the halomethyleneinium salt as the cyclizing agent.

14. A method according to claim 13 wherein the salt is formed from N-methylacetamide and phosphorus oxychloride and the solvent is toluene.

* * * * *